United States Patent [19]

Miller

[11] 4,396,259
[45] Aug. 2, 1983

[54] SPECTRUM GLASSES

[76] Inventor: Thomas H. Miller, 2061 Joy Rd., Pontiac, Mich. 48057

[21] Appl. No.: 313,235

[22] Filed: Oct. 20, 1981

[51] Int. Cl.³ .......................... G02C 7/10; G02C 1/00
[52] U.S. Cl. ...................................... 351/158; 351/41; 351/44
[58] Field of Search ...................... 351/44, 45, 47, 48, 351/158, 41; 46/1 F

[56] References Cited

U.S. PATENT DOCUMENTS 3,470,870 10/1969 Schoffer .
3,722,501 3/1973 Derouineau .
3,752,567 8/1973 Broadhurst .
3,867,020 2/1975 Braunhut .
3,972,319 8/1976 Dehlinger .
4,229,082 10/1980 Carreau .

Primary Examiner—John K. Corbin
Assistant Examiner—Rodney B. Bovernick
Attorney, Agent, or Firm—Basile, Weintraub & Hanlon

[57] ABSTRACT

Spectrum eyeglasses to provide a tranquilizing field of vision to the user are disclosed. The eyeglasses of the present invention comprise a frame mounted in front of the eyes of the user, an opaque wall supported by the frame positioned to prevent the entry of ambient light to the eye, a light source, a color wheel for selectively coloring light emitted from the light source, an opening formed in the opaque wall to expose the user's eye to a selectively varied field of color that is tranquilizing and sleep inducing.

7 Claims, 4 Drawing Figures

U.S. Patent     Aug. 2, 1983     4,396,259
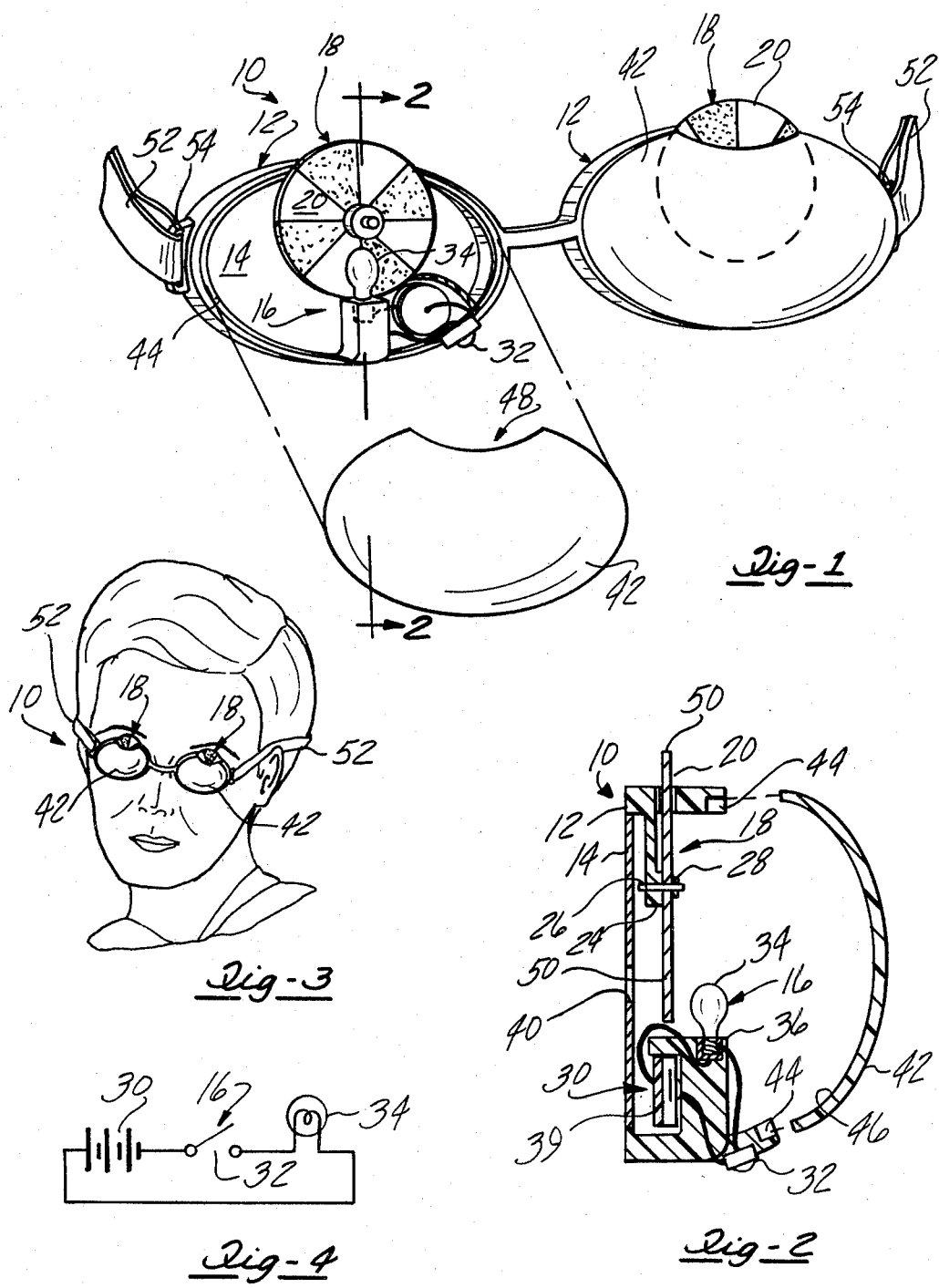

SPECTRUM GLASSES

BACKGROUND OF THE INVENTION

I. Field of the Invention

The present invention generally relates to the field of specialized eyeglasses and, in particular, the present invention is concerned with eyeglasses to provide a tranquilizing field of vision to the user. More specifically the present invention relates to the field of tranquilizing eyeglasses which provide a selectively varied field of vision in the form of a tranquilizing or sleep inducing color.

II. Description of the Prior Art

Tranquilizing or mood changing and relaxing devices utilizing a visual display are known. Generally, devices of this type comprise a box about the size of a television set which displays a tranquilizing scene which may include varying colors. Examples of non portable tranquilizing devices in the prior art are disclosed in the U.S. Pat. Nos. 3,470,870; 3,722,501. Eyeglasses having selectively varied lenses and or filters in the prior art are disclosed in the U.S. Pat. Nos. 3,752,567; 3,867,020; 3,972,319; and 4,229,082. These patents are relevant in that they disclose eyeglasses having selectively varied lenses. However, none of the above identified United States Patents disclose eyeglasses with selectively varied color with a self contained light source for providing the user with a tranquilizing field for inducing sleep and or relaxation. These patents are relevant to the Applicant's invention in that they represent the closest prior art relating to the present invention.

III. Prior Art Statement

The aforementioned prior art, in the opinion of the Applicant and the Applicant's Attorney, represents the closest prior art of which the Applicant and his Attorney are aware.

SUMMARY OF THE INVENTION

The present invention, which will be described in greater detail hereinafter comprises spectrum eyeglasses to provide a tranquilizing visual field to the user. The eyeglasses of the present invention comprise a frame mounted in front of the eyes of the user; an opaque wall supported by the frame positioned to prevent the entry of ambient light to the eye; a light source; and a color wheel for selectively coloring light emitted from the light source to provide the user with a selectively varied field of color that is tranquilizing and sleep inducing.

It is therefore an object of the present invention to provide new and improved spectrum eyeglasses.

It is a further object of the present invention to provide new and improved eyeglasses that have a tranquilizing visual field.

It is yet another object of the present invention to provide eyeglasses having a color wheel that provides a selectively variable field of color for the user.

It is a further object of the present invention to provide new and improved spectrum eyeglasses that have a self contained light source and are unaffected by ambient light conditions.

Further objects, advantages, and applications of the present invention will become apparent to those skilled in the art of tranquilizing visual devices when the accompanying description of one example of the best mode contemplated for practicing the invention is read in conjunction with the accompanying drawing.

BRIEF DESCRIPTION OF THE DRAWING

The description herein makes reference to the accompanying drawing wherein like reference numbers refer to like parts throughout the various several views, and wherein;

FIG. 1 illustrates a broken perspective exploded view of the spectrum eyeglasses of the present invention:

FIG. 2 illustrates a cross sectional view of the eyeglasses of FIG. 1 taken along the line 2—2 of FIG. 1;

FIG. 3 illustrates the eyeglasses of FIG. 1 as worn by the user; and

FIG. 4 illustrates an electrical diagram of the light source of the present invention.

DESCRIPTION OF THE PREFERRED EMBODIMENT

Referring now to the drawing, there is illustrated in FIGS. 1 and 2 one example of the present invention in the form of spectrum eyeglasses 10. The spectrum eyeglasses 10 are adapted to provide a tranquilizing visual field to the user to induce a relaxed condition or to aid the user in falling asleep. The eyeglasses 10 comprise a frame 12 mounted in front of the eyes of the user, an opaque wall 14 supported by the frame 12 and positioned to prevent the entry of ambient light to the eye, a light source 16, and a means 18 for selectively coloring the light emitted by the light source 16, wherein the wearer of the spectrum glasses 10 is provided a selectively varied field of color that is tranquilizing and sleep inducing.

The means 18 for selectively coloring the light emitted from the light source 18 comprises a color wheel 20 supported for rotation by the frame 12. A support 22 is formed integrally with the frame 12 and includes a hub 24 with a bore 26 passing therethrough. The bore 26 rotatably supports a shaft 28 which is attached to the center of the color wheel 20. The color wheel 20 is divided into a plurality of colors and hues by transparent pie-shaped sections. The wearer of the glasses may contact the perimeter of the color wheel 20 with his finger to rotate the color wheel and select a color most suitable to him. Colors that are generally most calming or tranquilizing to people are found to be pink, blue, and green. However, the practice of this invention is not limited to any particular color or hue.

As shown in FIG. 4 of the drawing the light source 16 comprises a battery 30, an "on" and "off" switch 32, a light bulb 34, and suitable wiring to interconnect the battery 38 by means of the "on-off" switch 32 to the light bulb 34 so that the light bulb 34 can be selectively switched on and off as required by the user. As shown in FIG. 2 of the drawing a light bulb 34 is mounted near the center of the opaque wall and is supported by a socket 36 which is integrally formed with the frame 12. A battery recess 38 is also cast integrally with the frame 12 to receive a minature battery such as the batterys employed in hearing aids and other minature devices. A battery cover 39 retains the battery in place and makes contact with the battery center terminal. The color wheel 20 is interposed between the light bulb 34 and the opaque wall 14 and an aperture 40 is formed centrally in the opaque wall to admit colored light to the space between the opaque wall 14 and the user's eye.

The spectrum eyeglasses of the present invention further include an outer opaque wall 42 which is snapped into a recess 44 formed along the perimeter of the frame 12. The outer opaque wall 42 further includes a light reflecting white inner surface 46 to enhance the light emitted by the light source 16. The outer opaque wall 42 includes an opening 48 to expose a portion of the color wheel 20 so that the user may contact the rim 50 of the color wheel with his finger to rotate the wheel to the desired color. An elastic strap 52 is provided with the strap extending around the back of the user's head to snugly secure the spectrum glasses to the users head and exclude ambient light. The strap 52 is secured to the frame by threading the strap through a pair of support openings 54 formed at the outer ends of the frame 12 with the ends of the strap 52 folded back upon themselves to form a loop. The free end of the loop is attached to the strap 52 by any suitable means such as adhesives, staples or rivets. The strap 52 and the outer opaque wall 42 protect the eyeglasses against damage when the user falls asleep.

It can thus be seen that the present invention has provided new and improved spectrum eyeglass for tranquilizing the user and aiding him in falling asleep.

It should be understood by those skilled in the art of tranquilizing devices that other forms of the Applicant's invention may be had all coming within the spirit of the invention and the scope of the appended claims.

Having thus described my invention what I claim is:

1. Spectrum eyeglasses to provide a tranquilizing visual field to the user comprising:
a frame mounted in front of the eyes of the user;
an opaque wall supported by said frame positioned to prevent the entry of ambient light to the eye;
a light source;
means for selectively coloring light emitted from said light source; and
wherein the user is provided a selectively varied field of color that is tranquilizing and sleep inducing.

2. The spectrum glasses as defined in claim 1 wherein the means for selectively coloring light emitted from said light source comprises;
a color wheel supported for rotation by said frame; and
said color wheel divided into a plurality of visually soothing colors.

3. The spectrum glasses as defined in claim 2 further comprising:
an outer opaque wall enclosing said light source.

4. The spectrum glasses as defined in claim 3 wherein said outer opaque wall includes a white inner surface to reflect and enhance said light source.

5. The spectrum glasses are defined in claim 3 further comprising:
an opening formed in said outer opaque wall; and
a portion of said color wheel projecting through said opening whereby a rim of said color wheel may be engaged to rotate said wheel and select a color.

6. The spectrum eyeglasses as defined in claim 1 wherein said light source comprises:
a threaded socket formed in said frame, a light bulb threadingly engaging said socket;
a battery receiving recess formed in said frame, a battery inserted into said battery receiving recess;
an "on-off" switch;
an electrical circuit directing electricity from one terminal of said battery through said switch, said light bulb and back to a second terminal of said battery; and
wherein when said switch is in an "on" position said light bulb is lighted, and when said switch is in an "off" position said light bulb is off.

7. The spectrum eyeglasses as defined in claim 1 further comprising an elastic strap attached to said frame and passing around the user's head to secure the glasses in place.

* * * * *